(12) United States Patent
Lawson Mohar

(10) Patent No.: US 9,435,182 B2
(45) Date of Patent: Sep. 6, 2016

(54) SYSTEM AND METHOD OF ASSESSING A WELLBORE SERVICING FLUID OR A COMPONENT THEREOF

(75) Inventor: Jeanie Lynn Lawson Mohar, Beasley, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 787 days.

(21) Appl. No.: 13/527,373

(22) Filed: Jun. 19, 2012

(65) Prior Publication Data

US 2013/0337491 A1    Dec. 19, 2013

(51) Int. Cl.
*C12Q 1/18* (2006.01)
*E21B 43/16* (2006.01)
*C12Q 1/64* (2006.01)

(52) U.S. Cl.
CPC .............. *E21B 43/16* (2013.01); *C12Q 1/64* (2013.01)

(58) Field of Classification Search
CPC ...... E21B 21/065; E21B 43/12; E21B 47/00; E21B 43/084; E21B 43/088; C09K 8/40; G01N 33/2823; G01N 2520/00
USPC .......................................................... 435/32
See application file for complete search history.

(56) References Cited

U.S. PATENT DOCUMENTS 2,091,023 A * 8/1937 Arterbury ..................... 175/210
7,081,437 B2 * 7/2006 Patel et al. ..................... 507/103

OTHER PUBLICATIONS

Methods for assessing the toxicity of sediment-associated contaminants with estuarine and marine amphipods. EPA. 1994.*
Foreign communication from a related counterpart application— International Search Report and Written Opinion, PCT/US2013/043932, Jun. 11, 2014, 11 pages.
Dorn, P.B., et al., "Development, Verification, and Improvement of a Sediment-Toxicity Test for Regulatory Compliance," XP055112963, SPE Drilling & Completion, Jun. 2007, pp. 90-97, Society of Petroleum Engineers.
EPA Supplemental Report, "Culturing Mysids (Mysidopsis bahia)," XP055113176, Sep. 1990, 24 pages, U.S. Environmental Protection Agency.
FAO Fisheries Technical Paper 361, "Manual on the production and use of live food for aquaculture, XP055120123, Zooplankton Grading," Laboratory of Aquaculture and Artemia Reference Center, Dec. 1996, 20 pages, Food and Agriculture Organization of the United Nations.
Uye, Shin-Ichi, et al., "Size Separation of Copepods by Sieving," XP055119993, 1983, pp. 136-140, vol. 39, Journal of the Oceanographical Society of Japan.

* cited by examiner

*Primary Examiner* — Lynn Y Fan

(57) ABSTRACT

A wellbore servicing fluid assessment method comprising introducing test organisms into a first section of a first tub, allowing organisms less than a first size to pass into a second section of the first tub, allowing organisms less than the first size to flow into a first section of a second tub, allowing organisms less than a second size to pass into a second section of the second tub, allowing organisms less than the second size to flow into a first section of a third tub, allowing organisms less than a third size to pass into a second section of the third tub, selecting test organisms of a desired testing size, dividing the selected test organisms into a control group and test group, subjecting the test group to the wellbore servicing fluid or a component, and assessing the acceptability of the wellbore servicing fluid or component.

20 Claims, 2 Drawing Sheets

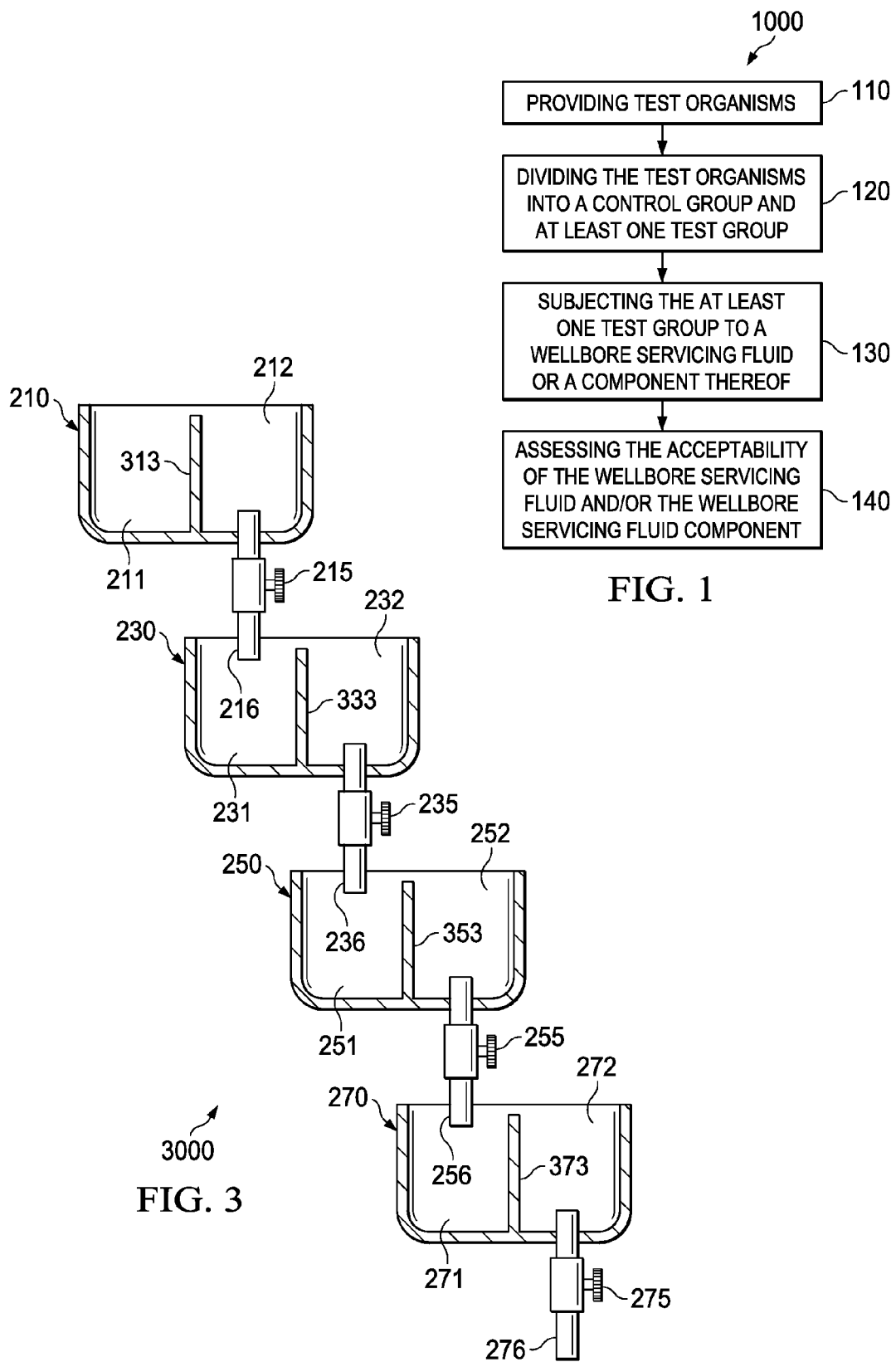

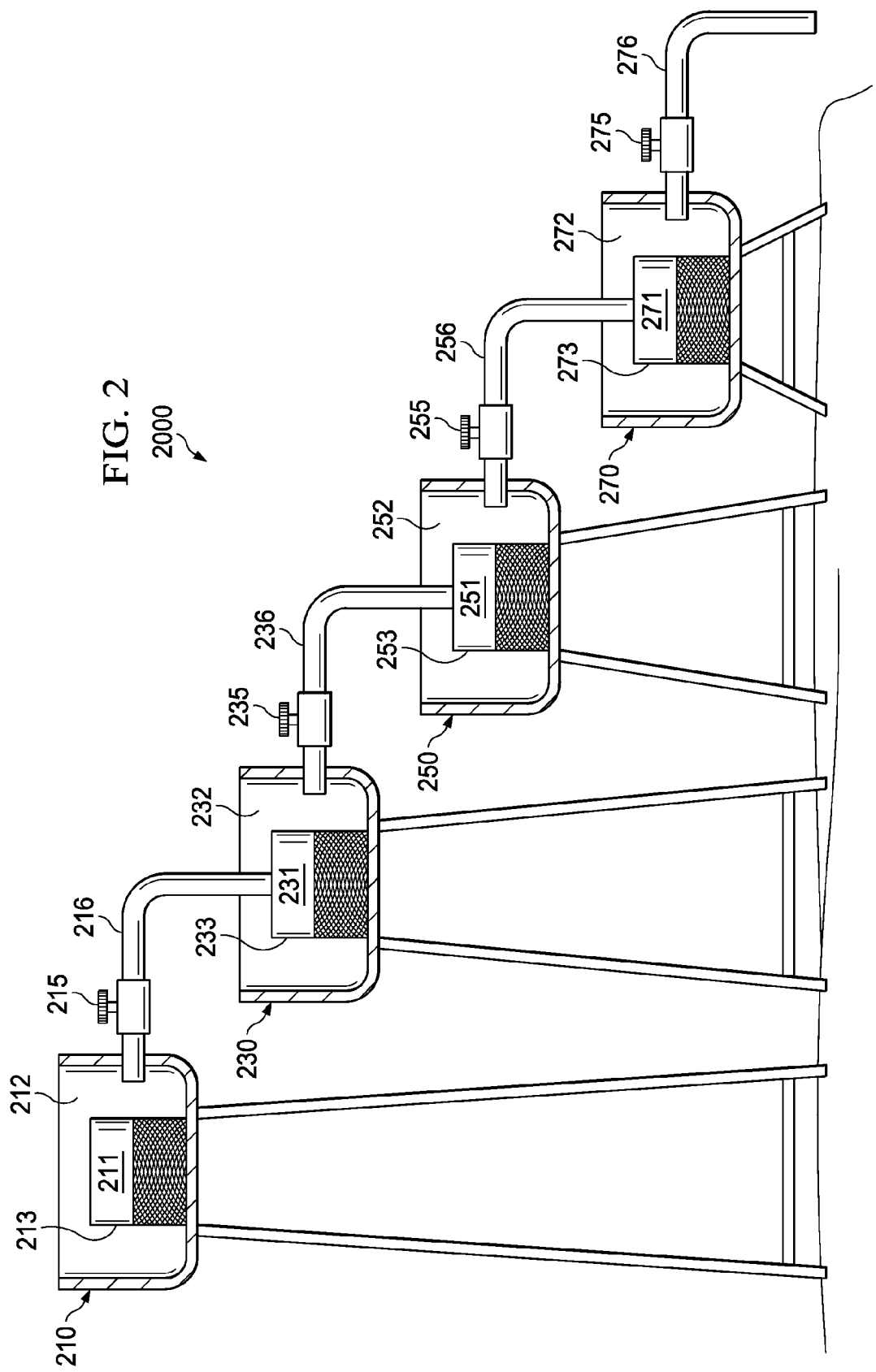

SYSTEM AND METHOD OF ASSESSING A WELLBORE SERVICING FLUID OR A COMPONENT THEREOF

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Hydrocarbons, such as oil and gas, are often produced from wells that penetrate hydrocarbon-bearing subterranean formations or portions thereof. Conventionally, a subterranean formation is prepared for the production of oil and/or gas therefrom by drilling a wellbore into the subterranean formation. During the drilling operation, a drilling fluid is circulated through the wellbore to remove cuttings and cool and lubricate the drilling apparatus. After the wellbore has been drilled to a preferred depth, it is common to complete the wellbore by cementing a casing string within the wellbore. Cementing is conventionally accomplished by pumping a cementitious composition into an annular space between the casing and wellbore walls and allowing the composition to set in place.

Further, completed, partially completed, and/or uncompleted wellbores are often serviced by stimulation operations to improve the recovery of hydrocarbons therefrom. Such stimulation operations include hydraulic fracturing operations, acidizing treatments, perforating operations, or the like. Stimulation operations often involve introducing various wellbore servicing fluids into at least some part of the subterranean formation at various rates, pressures, and/or amounts.

Further still, other wellbore servicing operations may be necessary throughout the service life of a wellbore and thereafter, for example, clean-out operations, fluid-loss control operations, a well containment operation, a well-kill operation, or the like. Similarly, such additional servicing operations may also entail introducing servicing fluids into the subterranean formation, for example, to increase production from the wellbore, to isolate a zone or segment of the subterranean formation, to cease the production of fluids from the subterranean formation, or for some other purpose.

Therefore, as will be appreciated by one of skill in the art, during the life of a well, many of the operations performed with respect to a wellbore involve the introduction of various fluids into the wellbore and/or the subterranean formation. The introduction of fluids presents the opportunity for such fluids to enter the environment, such as, by mixing and/or intermingling with fluids that may be present within the formation, for example, groundwater. In addition, when wellbores are drilled into a formation beneath a body of water, such as a lake, sea, or ocean, there is also the opportunity for wellbore fluids to become mixed with that water. Thus, because wellbore fluids may come into contact with the environment, it is necessary to assess the environmental impact associated with any such fluids and/or the components thereof prior to utilizing the wellbore fluid and to ensure such fluid can safely be employed for its intended purpose.

Accordingly, there exists a need for a method and/or system for assessing the environmental impact of a wellbore servicing fluid or a component thereof.

SUMMARY

Disclosed herein is a method of assessing a wellbore servicing fluid or a component thereof comprising providing a plurality of test organisms, wherein providing the plurality of test organisms comprises introducing at least a portion of a population of the test organisms into a first section of a first tub, wherein the first section of the first tub is separated from a second section of the first tub by a first screen, wherein the first screen is configured to retain an organism of at least a first size and to allow passage of an organism less than the first size, allowing at least a portion of the organisms of a size less than the first size to pass through the first screen and into the second section of the first tub, allowing at least a portion of the organisms of a size less than the first size to flow out of the first tub and into a first section of a second tub, wherein the first section of the second tub is separated from a second section of the second tub by a second screen, wherein the second screen is configured to retain an organism of at least a second size and to allow passage of an organism less than the second size, allowing at least a portion of the organisms of a size less than the second size to pass through the second screen and into the second section of the second tub, allowing at least a portion of the organisms of a size less than the second size to flow out of the second tub and into a first section of a third tub, wherein the first section of the third tub is separated from a second section of the third tub by a third screen, wherein the third screen is configured to retain an organism of at least a third size and to allow passage of an organism less than the third size, allowing at least a portion of the organisms of a size less than the third size to pass through the third screen and into the second section of the third tub, and allowing at least a portion of the organisms of a size less than the third size to flow out of the third tub, selecting test organisms of a size desired for testing from the first section of the first tub, the first section of the second tub, the first section of the third tub, or combinations thereof, dividing the test organisms of the selected size into a control group and at least one test group, subjecting the at least one test group to the wellbore servicing fluid or component thereof, and assessing the acceptability of the wellbore servicing fluid or component thereof.

BRIEF DESCRIPTION OF THE DRAWINGS

For a more complete understanding of the present disclosure and the advantages thereof, reference is now made to the following brief description, taken in connection with the accompanying drawings and detailed description:

FIG. 1 is a diagram of an embodiment of a wellbore fluid assessment method;

FIG. 2 is a schematic of a first embodiment of a wellbore fluid assessment system; and FIG. 3 is a schematic of a second embodiment of a wellbore fluid assessment system.

DETAILED DESCRIPTION OF THE EMBODIMENTS

In the drawings and description that follow, like parts are typically marked throughout the specification and drawings with the same reference numerals, respectively. The drawing figures are not necessarily to scale. Certain features of the invention may be shown exaggerated in scale or in somewhat schematic form and some details of conventional elements may not be shown in the interest of clarity and conciseness. The present invention is susceptible to embodiments of different forms. Specific embodiments are described in detail and are shown in the drawings, with the understanding that the present disclosure is not intended to limit the invention to the embodiments illustrated and described herein. It is to be fully recognized that the different teachings of the embodiments discussed herein may be employed separately or in any suitable combination to produce desired results.

Unless otherwise specified, use of the terms "connect," "engage," "couple," "attach," or any other like term describing an interaction between elements is not meant to limit the interaction to direct interaction between the elements and may also include indirect interaction between the elements described.

Unless otherwise specified, use of the terms "up," "upper," "upward," "up-hole," "upstream," or other like terms shall be construed as generally from the formation toward the surface or toward the surface of a body of water; likewise, use of "down," "lower," "downward," "down-hole," "downstream," or other like terms shall be construed as generally into the formation away from the surface or away from the surface of a body of water, regardless of the wellbore orientation. Use of any one or more of the foregoing terms shall not be construed as denoting positions along a perfectly vertical axis.

Unless otherwise specified, use of the term "subterranean formation" shall be construed as encompassing both areas below exposed earth and areas below earth covered by water such as ocean or fresh water.

Disclosed herein are embodiments of methods, and the associated apparatuses and systems, of assessing the environmental impact of a wellbore servicing fluid or a component thereof. Referring to FIG. 1, an embodiment of a wellbore fluid assessment (WFA) method 1000 is illustrated in schematic form. In the embodiment of FIG. 1, the WFA method 1000 generally comprises the steps of providing test organisms 110, dividing the test organisms into a control group and at least one test group 120, subjecting the at least one test group to a wellbore servicing fluid or a component thereof 130, and assessing the acceptability of the wellbore servicing fluid and/or the wellbore servicing fluid component 140. Also disclosed herein is a method of servicing a wellbore. In an embodiment, such a wellbore servicing method generally comprises, after assessing the acceptability of a wellbore servicing fluid or a component thereof, for example, as by the WFA method disclosed herein, communicating the wellbore servicing fluid and/or a wellbore servicing fluid comprising the wellbore servicing fluid component into a wellbore.

In an embodiment, the step of providing the test organisms 110 generally comprises the process by which a suitable number of one or more suitable test organisms is made available for use in the remainder of the WFA method 1000. In an embodiment, the step of providing the test organisms may generally comprise the sub-steps of culturing a population of test organisms and selecting organisms for use in the WFA method 1000 from the population of test organisms.

In an embodiment, a suitable test organism may be characterized as an aquatic and/or marine organism. In an embodiment, a suitable test organism may be an organism whose suitability for testing, as will be disclosed herein, is dependent upon size.

In a particular embodiment, the test organism may comprise *Leptocheirus plumulosus* (*L. plumulosus*). *L. plumulosus* is an amphipod native to brackish, subtidal waters. *L. plumulosus* may be characterized as a relatively large amphipod having a generally cylindrical body and being generally brownish-grey in color with dark bands. *L. plumulosus* feed on particulate matter either in suspension or on the surface of sediment material. Although one or more of the embodiments may disclose the WFA method 1000 or a portion thereof with respect to *L. plumulosus*, this application should not be construed as so limited. One of skill in the art viewing this disclosure with appreciate that any suitable test organism may be employed in the WFA method 1000. An alternative example of a suitable test organism includes, but is not limited to *Corophium volutator*, which is a sediment-dwelling amphipod.

In an embodiment, the test organisms may be provided and/or present within a suitable fluid and/or composition, referred to herein as an environmental fluid. In such an embodiment, the environmental fluid in which the test organisms are provided generally refers to a fluid and/or composition that is substantially similar to the natural environment of the a given test organism. For example, in various embodiments, the test organisms may be provided within an aqueous solution (e.g., water). In an embodiment, the aqueous solution may comprise sediment (e.g., mud), as may be appropriate for a given organism. For example, some test organisms may dwell within the sediment beneath a volume of water. In an embodiment where the test organisms are provided within such an aqueous solution (e.g., water and/or mud), the water (and/or the water used to form the mud) may be characterized as any suitable wholly and/or substantially aqueous fluid. In such an embodiment, such a substantially aqueous fluid comprises less than about 50% nonaqueous component(s), alternatively less than about 45%, 40%, 35%, 30%, 25%, 20%, 15%, 10%, 5%, 4%, 3%, 2% or 1% nonaqueous component(s). In an embodiment, the water may comprise an inorganic monovalent salt, an inorganic multivalent salt, or both. Nonlimiting examples of salts as may be present within the water include water-soluble chloride, bromide and carbonate, hydroxide and formate salts of alkali and alkaline earth metals, zinc bromide, and combinations thereof. The salt or salts in the water may be present in an amount ranging from greater than about 0.01% by weight to a saturated salt solution. In a particular embodiment, the salt or salts in the water may be present in an amount ranging from about 5% to about 25% by weight; alternatively, about 20% by weight.

Referring to FIGS. 2 and 3, a first and second embodiment, respectively, of a test organism collection and separation (TOCS) system 2000 and 3000, respectively, for use in the step of providing the test organisms 110, particularly, for use in either or both of the sub-steps of culturing a population of test organisms and the sub-step of selecting organisms for use in the WFA method 1000, are illustrated. In the embodiments of FIGS. 2 and 3, the TOCS systems 2000 and 3000, respectively, are generally configured for culturing the test organisms and allowing the selection of some portion of the test organisms on the basis of size.

In the embodiment of FIGS. 2 and 3, the TOCS systems 2000 and 3000 each comprise a first tub 210, a second tub 230, a third tub 250, and a fourth tub 270. Additionally, in an embodiment, a TOCS system like TOCS system 2000 and/or 3000 may further comprise a fourth tub, a fifth tub, a sixth tub, or any suitable number of additional tubs, as will be appreciated by one of skill in the art viewing this disclosure.

In the embodiments of FIGS. 2 and 3, the first tub 210 comprises a first section 211 and a second section 212, the second tub 230 comprises a first section 231 and a second section 232, the third tub 250 comprises a first section 251 and a second section 252, and the fourth tub 270 comprises a first section 271 and a second section 272. In each of the first, second, third, and fourth tubs, 210, 230, 250, and 270, respectively, the first section (i.e., 211, 231, 251, and/or 271, respectively) of any particular tub may be separated from the second section (i.e., 212, 232, 252, and/or 272, respectively) by a suitable divider, 213/313, 233/333, 253/353, and/or 273/373, respectively.

In the embodiment of FIG. 2, the first section 211, 231, 251, and/or 271 may be defined entirely by the divider 213, 233, 253, and/or 273. For example, in such an embodiment, the divider 213, 233, 253, and/or 273 may be substantially configured as a sieve or the like, for example, a cylindrical sieve, such as a mesh cylindrical sleeve. Referring to FIG. 3, an alternative configuration of a divider is illustrated. In the embodiment of FIG. 3, the first section 211, 231, 251, and/or 271 is defined partially by the divider 313, 333, 353, and/or 373 and partially by the walls of the tub. For example, in such an embodiment, the divider 313, 333, 353, and/or 373 may be substantially configured as a wall or the like.

In an embodiment, a divider may be free-standing. Alternatively, a divider may be attached to walls of tub. Also, in an embodiment, a divider may be characterized as removable. Alternatively, a divider may be characterized as permanent and/or semi-permanent. For example, in the embodiment of FIG. 2 where the dividers 213, 233, 253, and 273 are configured as sieves (e.g., generally cylindrical sieves), the sieves are unattached and are readily removable. An example of sieves suitable for use herein includes, but is not limited to, those commercially available through Carolina Biological Supply Company in Burlington, N.C. Alternatively, in the embodiment of FIG. 3 where the dividers 313, 333, 353, and 373 are configured as walls, the walls are attached to the walls of each of the respective tubs and are not removable.

In an embodiment, a divider like dividers 213, 233, 253, and/or 273 or like dividers 313, 333, 353, and/or 373 may be configured to separate material on the basis of size, for example, by retaining matter of a given size while allowing the passage of matter of a smaller size. For example, in the embodiments of FIGS. 2 and 3, each of the dividers 213/313, 233/333, 253/353, and 273/373 comprises a mesh material or fabric such as a screen or the like. In an embodiment, such a mesh material may generally comprise any suitable type or configuration of mesh. Examples of suitable mesh materials may include, but are not limited to, plastic fibers, metallic fibers, wires, natural fibers, the like, or combinations thereof.

In an embodiment, the screens comprising the dividers may each, independently, be characterized as having a suitable mesh size. As used herein, the term "mesh size" is used to refer to the sizing of a particular screen as defined by as "ASTM E-11 Specifications" or "ISO 3310-1". Generally, mesh size may refer approximately to the greatest size of material (e.g., test organism) that will pass through a particular mesh size, for example, the nominal opening. The mesh size may also refer to the inside dimension of each opening in the mesh (e.g., the inside diameter of each square).

In an embodiment, the mesh size of each screen may become progressively smaller in comparison to the screen immediately before, moving from the first tub 210 to the second tub 230, from the second tub 230 to the third tub 250, and from the third tub 250 to the fourth tub 270. That is, the first screen may comprise, comparatively, the largest mesh size, the second screen may comprise the second largest mesh size, the third screen may comprise the third largest mesh size, and the fourth screen comprises the fourth largest mesh size. Therefore, in such an embodiment, the progressively smaller mesh sizes may be configured so as to retain progressively smaller matter.

For example, in an embodiment, the first screen may comprise a mesh size of 1,000 microns, the second screen may comprise a mesh size of 710 microns, the third screen may comprise a mesh size of 500 microns, and the fourth screen may comprise a mesh size of 300 microns. In an alternative embodiment where a TOCS system comprises a fifth tub comprising a fifth divider and a fifth screen, the first screen may comprise a mesh size of 1,000 microns, the second screen may comprise a mesh size of 850 microns, the third screen may comprise a mesh size of 710 microns, the fourth screen may comprise a mesh size of 500 microns, and the fifth screen may comprise a mesh size of 300 microns. One of skill in the art will appreciate that any suitable size and/or number of screen(s) or the like may be employed in the TOCS system 2000 and/or 3000.

In an embodiment, each of the first, second, third, and fourth tubs, 210, 230, 250, and 270, respectively, is configured to selectively allow fluid outflow therefrom. For example, in the embodiments of FIGS. 2 and 3, each of the first, second, third, and fourth tubs, 210, 230, 250, and 270, respectively, comprises a valve, 215, 235, 255, and/or 275, respectively, and a flow conduit, 216, 236, 256, and/or 276, respectively. In the embodiments of FIGS. 2 and 3, the valves (215, 235, 255, and/or 275) and flow conduits (216, 236, 256, and/or 276) are configured to convey fluid from the second section of a particular tub into the first section of an adjacent, relatively downstream tub. For example, the first valve 215 and first conduit 216 are configured to convey fluid from the second section 212 of the first tub 210 into the first section 231 of the second tub 230; the second valve 235 and the second conduit 236 are configured to convey fluid from the second section 232 of the second tub 230 into the first section 251 of the third tub 250; and the third valve 255 and the third conduit 256 are configured to convey fluid from the second section 252 of the third tub 250 into the first section 271 of the fourth tub 270. Similarly, the fourth valve 275 and the fourth conduit 276 may be configured to convey fluid from the second section 272 of the fourth tub 270 into a suitable fluid receptacle, for example a sink, drain, or basin.

The valve may comprise any suitable type or configuration of valve. Examples of suitable types and configurations of valves include, but are not limited to ball valves, gate valves, disc valves, butterfly valves, globe valves, or the like. In an embodiment, each of the valves, 215, 235, 255, and/or 275 may be in fluid communication with the reservoir of the first tub 210, the second tub 230, the third tub 250, and the fourth tub 270, respectively. Particularly, the valves 215, 235, 255, and/or 275 may be in fluid communication with the second section of each of the respective tubs. For example, as shown in the embodiment of FIG. 2, each of the valves may be positioned within a side-wall of each of the respective tubs. In an embodiment, one of more of the valves may be positioned a suitable distance above the bottom of each of the respective tubs.

Alternatively, as shown in the embodiment of FIG. 3, the valve may be placed in the bottom of each of the respective tubs. Also in the embodiment of FIG. 3, the valve may comprise an inlet that extends a suitable distance above the bottom of each of the respective tubs. As such, in either the embodiment of FIG. 2 or the embodiment of FIG. 3, a fluid of a depth greater than or equal to the height of the position in the wall of the tub of the valve (in FIG. 2) or the height of the inlet (in FIG. 3) within the second section of each of the respective tubs may flow into and/or via each of the respective valves. Also, in either the embodiment of FIG. 2 or the embodiment of FIG. 3, an amount of fluid (e.g., a fluid of a depth lesser than or equal to the height of the position in the wall of the tub of the valve (in FIG. 2) or the height of the inlet (in FIG. 3)) may remain in the tubs. As such, the tubs may be configured to retain a desired amount of fluid, for example, such that the tubs are not completely emptied upon drainage.

In an embodiment, each of the flow conduits may comprise any suitable type and/or size of such flow conduit. Examples of suitable types of flow conduits include, but are not limited to, pipes, hoses, or combinations thereof. The flow conduits 216, 236, 256, and/or 276 may be permanently, semi-permanently, and/or removably coupled (e.g., via a glued, threaded, or fitted connection) to the outlet of the valves, 215, 235, 255, and/or 275, respectively. The flow conduits 216, 236, 256, and/or 276 may be of a suitable length to allow the fluid be conveyed therethrough to reach and/or flow into the adjacent tub or container. In an embodiment, the flow conduits may be of sufficient length to allow the fluid to flow into such tub and/or container at an angle (e.g., such that the fluid flowing into the tub and/or container at an angle less than perpendicular).

In an embodiment, the first, second, third, and fourth tubs, 210, 230, 250, and 270, respectively, may each be positioned at a suitable height, for example, a height allowing for flow of a fluid by gravity from one tub to another. In an embodiment, each tub may be positioned at a progressively lower height in comparison to the tub immediately before, moving from the first tub 210 to the second tub 230, from the second tub 230 to the third tub 250, and from the third tub 250 to the fourth tub 270. That is, the first tub 210 may be positioned at the greatest height, the second tub 230 at the second greatest height, the third tub 250 at the third greatest height, and the fourth tub 270 at the fourth greatest height. The difference in height between any two adjacent tubs may be any suitable distance as may be determined by one of skill in the art viewing this disclosure. The tubs may be positioned on platform suitable to support the tub; alternatively, the tubs may be fitted with any suitable configuration of legs, stands, or the like.

In an embodiment, a TOCS system like TOCS system 2000 and/or 3000 may be employed in one or more of culturing the test organisms and separating the test organisms on the basis of size. In such an embodiment, culturing the test organisms and/or separating the test organisms on the basis of size may comprise the steps of introducing a fluid comprising at least a portion of the population of the test organisms into the first section of the first tub and allowing at least a portion of the organisms to pass through the first screen and into the second section of the first tub. As will be appreciated by one of ordinary skill in the art, only those organisms having a size of about less than, alternatively, about equal to or less than, the first mesh size will be capable of passing through the first screen and into the second section of the first tub. Organisms having a size about greater than, alternatively, about equal to or greater than, the first mesh size will be retained within the first section of the first tub. In an embodiment, allowing the organisms to pass through the first screen and into the second section of the first tub may further comprise rinsing the first screen to facilitate movement of the organisms therethrough.

In an embodiment, culturing the test organisms and/or selecting the test organisms on the basis of size may further comprise allowing at least a portion of the test organisms, for example, within the fluid, in the second section of the first tub to flow out of the first tub and into the first section of the second tub. In such an embodiment, the organisms within the second section of the first tub, or a portion thereof, may be allowed to flow into the first section of the second tub via first valve 215 and the first flow conduit 216. For example, an operator may allow the fluid and the organisms within the second section of the first tub to flow into the first section of the second tub by providing a route of fluid communication via the first valve and the first flow conduit, for example, by opening the first valve. With the first valve open, the fluid and the organisms within the second section of the first tub may flow therefrom and into the first section of the second tub. As will be appreciated by one of skill in the art, because the first tub is positioned at a height greater than the height of the second tub, the fluid and organisms will readily flow, for example, by gravity, into the second tub.

In an embodiment, culturing the test organisms and/or selecting the test organisms on the basis of size may further comprise allowing at least a portion of the organisms to pass through the second screen and into the second section of the second tub. As will be appreciated by one of ordinary skill in the art, only those organisms having a size of about less than, alternatively, about equal to or less than, the second mesh size will be capable of passing through the second screen and into the second section of the second tub. Organisms having a size about greater than, alternatively, about equal to or greater than, the second mesh size will be retained within the first section of the second tub. In an embodiment, allowing the organisms to pass through the second screen and into the second section of the second tub may further comprise rinsing the second screen to facilitate movement of the organisms therethrough.

In an embodiment, culturing the test organisms and/or selecting the test organisms on the basis of size may further comprise allowing at least a portion of the test organisms, for example, within the fluid, in the second section of the second tub to flow out of the second tub and into the first section of the third tub. In such an embodiment, the organisms within the second section of the second tub, or a portion thereof, may be allowed to flow into the first section of the third tub via second valve 235 and the second flow conduit 236. For example, an operator may allow the fluid and the organisms within the second section of the second tub to flow into the first section of the third tub by providing a route of fluid communication via the second valve and the second flow conduit, for example, by opening the second valve. With the second valve open, the fluid and the organisms within the second section of the second tub may flow therefrom and into the first section of the third tub. As will be appreciated by one of skill in the art, because the second tub is positioned at a height greater than the height of the third tub, the fluid and organisms will readily flow, for example, by gravity, into the third tub.

In an embodiment, culturing the test organisms and/or selecting the test organisms on the basis of size may further comprise allowing at least a portion of the organisms to pass through the third screen and into the second section of the third tub. As will be appreciated by one of ordinary skill in the art, only those organisms having a size of about less than, alternatively, about equal to or less than, the third mesh size will be capable of passing through the third screen and into the second section of the third tub. Organisms having a size about greater than, alternatively, about equal to or greater than, the third mesh size will be retained within the first section of the third tub. In an embodiment, allowing the organisms to pass through the third screen and into the second section of the third tub may further comprise rinsing the third screen to facilitate movement of the organisms therethrough.

In an embodiment, culturing the test organisms and/or selecting the test organisms on the basis of size may further comprise allowing at least a portion of the test organisms, for example, within the fluid, in the second section of the third tub to flow out of the third tub and into the first section of the fourth tub. In such an embodiment, the organisms within the second section of the third tub, or a portion thereof, may be allowed to flow into the first section of the fourth tub via third valve 255 and the third flow conduit 256. For example, an operator may allow the fluid and the organisms within the second section of the third tub to flow into the first section of the fourth tub by providing a route of fluid communication via the third valve and the third flow conduit, for example, by opening the third valve. With the third valve open, the fluid and the organisms within the second section of the third tub may flow therefrom and into the first section of the fourth tub. As will be appreciated by one of skill in the art, because the third tub is positioned at a height greater than the height of the fourth tub, the fluid and organisms will readily flow, for example, by gravity, into the fourth tub.

In an embodiment, culturing the test organisms and/or selecting the test organisms on the basis of size may further comprise allowing at least a portion of the organisms to pass through the fourth screen and into the second section of the fourth tub. As will be appreciated by one of ordinary skill in the art, only those organisms having a size of about less than, alternatively, about equal to or less than, the fourth mesh size will be capable of passing through the fourth screen and into the second section of the fourth tub. Organisms having a size about greater than, alternatively, about equal to or greater than, the fourth mesh size will be retained within the first section of the fourth tub. In an embodiment, allowing the organisms to pass through the fourth screen and into the second section of the fourth tub may further comprise rinsing the fourth screen to facilitate movement of the organisms therethrough.

In an additional embodiment, for example, in an embodiment where the TOCS system comprises a fifth tub, culturing the test organisms and/or selecting the test organisms on the basis of size may further comprise allowing at least a portion of the test organisms, for example, within the fluid, in the second section of the fourth tub to flow out of the fourth tub and into the first section of the fifth tub. In such an embodiment, the organisms within the second section of the fourth tub, or a portion thereof, may be allowed to flow into the first section of the fifth tub via the fourth valve 275 and the fourth flow conduit 276. For example, an operator may allow the fluid and the organisms within the second section of the fourth tub to flow into the first section of the fifth tub by providing a route of fluid communication via the fourth valve and the fourth flow conduit, for example, by opening the fourth valve. With the fourth valve open, the fluid and the organisms within the second section of the fourth tub may flow therefrom and into the first section of the fifth tub. As will be appreciated by one of skill in the art, because the fourth tub is positioned at a height greater than the height of the fifth tub, the fluid and organisms will readily flow, for example, by gravity, into the fifth tub.

In such an embodiment, culturing the test organisms and/or selecting the test organisms on the basis of size may further comprise allowing at least a portion of the organisms to pass through the fifth screen and into the second section of the fifth tub. As will be appreciated by one of ordinary skill in the art, only those organisms having a size of about less than, alternatively, about equal to or less than, the fifth mesh size will be capable of passing through the fifth screen and into the second section of the fifth tub. Organisms having a size about greater than, alternatively, about equal to or greater than, the fifth mesh size will be retained within the first section of the fifth tub. In an embodiment, allowing the organisms to pass through the fifth screen and into the second section of the fifth tub may further comprise rinsing the fifth screen to facilitate movement of the organisms therethrough.

In an embodiment, the water, mud, sediment, and/or other materials present within the second section of the terminal tub (e.g., the fourth tub in an embodiment where the TOCS system comprises four tubs, alternatively, the fifth tub in an embodiment where the TOCS system comprises five times) may be removed, discarded, placed within another suitable receptacle, for example, by allowing such materials to flow out of that tub, for example, via the valve and conduit.

In an embodiment, as may be appreciated by one of skill in the art viewing this disclosure, upon culturing the test organisms and/or separating the test organisms on the basis of size, for example, as by use of a TOCS system as disclosed herein, the test organisms may be present within a plurality of groups, approximately, on the basis of size. For example, in an embodiment where the TOCS system comprises four tubs, the test organisms may be present in four groups. In an embodiment where the first screen comprises a mesh size of 1,000 microns, the second screen comprises a mesh size of 710 microns, the third screen comprises a mesh size of 500 microns, and the fourth screen comprises a mesh size of 300 microns, the first group (e.g., which may be present within the first section of the first tub) may be characterized as having a size of greater than about 1,000 microns, the second group (e.g., which may be present within the first section of the second tub) may be characterized as having a size of less than about 1000 microns and greater than about 710 microns, the third group (e.g., which may be present within the first section of the third tub) may be characterized as having a size of less than about 710 microns and greater than about 500 microns, and the fourth group (e.g., which may be present within the first section of the fourth tub) may be characterized as having a size of less than about 500 microns and greater than about 300 microns.

Alternatively, in an embodiment where the TOCS system comprises five tubs, the test organisms may be present in five groups. In an embodiment where the first screen comprises a mesh size of 1,000 microns, the second screen comprises a mesh size of 850 microns, the third screen comprises a mesh size of 710 microns, the fourth screen comprises a mesh size of 500 microns, and the fifth screen comprises a mesh size of 300 microns, the first group (e.g., which may be present within the first section of the first tub) may be characterized as having a size of greater than about 1,000 microns, the second group (e.g., which may be present within the first section of the second tub) may be characterized as having a size of less than about 1000 microns and greater than about 850 microns, the third group (e.g., which may be present within the first section of the third tub) may be characterized as having a size of less than about 850 microns and greater than about 710 microns, the fourth group (e.g., which may be present within the first section of the fourth tub) may be characterized as having a size of less than about 710 microns and greater than about 500 microns, and the fifth group (e.g., which may be present within the first section of the fifth tub) may be characterized as having a size of less than about 500 microns and greater than about 300 microns.

In an embodiment, a suitable number of test organisms within a given size range may be selected for testing. For example, as may be appreciated by one of skill in the art viewing this disclosure, the size and/or number of test organisms that will be suitable for a given test procedure may vary depending upon a variety of factors, such as, the number of trials to be performed, the duration of the trials, the type of wellbore fluid or wellbore fluid component to be assessed, the means by which the fluid is to be assessed (e.g., as will be discussed herein below) or the like. As such, in various embodiments, one of skill in the art viewing this disclosure may select test organisms from one or more of the groups of test organisms. For example, one of skill in the art viewing this disclosure may select test organisms from any one or more of the first group, the second group, the third group, the fourth group, and/or the fifth group, as disclosed about. As will be appreciated by one of skill in the art viewing this disclosure, the number of tubs, the configuration of tubs, and/or the mesh size of the screens employed within each of those tubs may be varied in order to achieve groupings of test organisms in a particular or desired range or ranges.

In an embodiment, the test organisms not selected for usage in the trials, as will be described herein below, may be returned to a suitable culturing environment, retained in separate groupings (e.g., according to size), utilized as brood stock for continued culturing of such test organisms, or the like.

In an embodiment, the test organisms selected for usage in the trial(s) may be divided into a plurality of groups comprising a control group and one or more test groups. For example, in various embodiments the test organisms, for a given trial, may be divided into a control group and one, two, three, four, five, or more test groups. In such an embodiment, each of the plurality of test groups may be used to test varying concentrations of the wellbore servicing fluid and/or component, different components of a single wellbore servicing fluid, or the like. As referred to herein, the wellbore servicing fluid and/or component generally refers to a fluid (e.g., a composite fluid comprising multiple components) or one or more components thereof, which may be similar in composition, concentration, or combinations thereof, to a fluid as may be employed in the performance of a wellbore servicing operation, for example, a drilling fluid, a wellbore clean-out fluid, a completion and/or cementing fluid, an acidizing fluid, a perforating fluid, a fracturing or other stimulation fluid, a workover fluid, a shut-in or well-kill fluid, any other like, suitable fluid.

For example, a plurality of test groups may be utilized to test the acceptability of a given servicing fluid and/or a given servicing fluid component at about 20%, 40%, 60%, 80%, 100%, and/or 120%, respectively, of the concentration at which that fluid and/or component may be employed. In another embodiment, a plurality of test groups may be utilized to test the acceptability of Component A, Component B, Component C, and Component D, etc., respectively, of a given servicing fluid.

As will be appreciated by one of skill in the art viewing this application, each trial may be performed in multiple iterations, for example, to improve the accuracy and/or statistical significance of any such trials. For example, the trials, as disclosed herein, may be performed in duplicate, triplicate, quadruplicate, etc. In such an embodiment, one of skill in the art will appreciate that the number of test organisms necessitated by such multiple trial iterations will increase, correspondingly.

In an embodiment, each of the control group and the one or more test groups may be placed in separate, suitable test containers for the duration of the trials. Such test containers may be selected based upon factors including, but not limited to, the test organism that was selected, the size of the test organisms, the number of test organisms, the duration of the trial, the suitability of the environment provided by the test container for the test organisms, the amount of fluid and/or material to be tested, the like, and combinations thereof. Depending upon such factors, examples of suitable test containers may include, but are not limited to, petri dishes, jars of various sizes and configurations, trays, tubs, barrels, and the like.

As noted above, in an embodiment the control group and the test group may be provided in a suitable environmental fluid or sediment. In an embodiment, the test group or groups of the test organisms may be subjected to the wellbore servicing fluid or a component thereof, for example, by introducing the wellbore servicing fluid and/or component into the environmental fluid. As noted above, in an embodiment, the test groups may be subjected to the wellbore servicing fluid and/or wellbore servicing fluid component in varying concentrations and/or the test groups may be subjected to varying components thereof.

In an embodiment, each of the one or more test groups may be placed in the environmental fluid, along with the servicing fluid and/or servicing fluid component in a specified concentration, within the test container for a suitable duration. For example, such a suitable duration may be about 24 hours, alternatively, about 48 hours, alternatively, about 72 hours, alternatively, about 5 days, alternatively, about 7 days, alternatively, about 10 days, alternatively, about 12 days, alternatively, about 15 days, alternatively, about 28 days. One of ordinary skill in the art viewing this disclosure will appreciate that the apparatuses, systems, and/or methods disclosed herein may be similarly employed in a trial having any suitable duration.

In an embodiment, the environment within each of the test containers may be maintained as will be suitable for the selected test organism. For example, in various embodiments, maintaining such a suitable environment may include maintaining a suitable temperature (e.g., about 20° C.), maintaining the salinity of the environmental fluid within a suitable range (e.g., about 20% salinity), maintaining the oxygen saturation of the environmental fluid within a suitable range (e.g., via aeration), provision of food sources and/or nutrients, or combinations thereof.

In an embodiment, the acceptability of the wellbore servicing fluid and/or the wellbore servicing fluid component may be assessed upon completion of the trial (e.g., at the termination of the desired duration). In an embodiment, assessing the acceptability of the fluid and/or the fluid component may comprise assessing the health of the test organisms of the at least one test group and assessing the health of the test organisms of the control group. In such an embodiment, assessing the health of the test organisms may comprise observing the survival rate associated with each group, observing the reproduction rate associated with each group, the rate of weight change associated with each group, observing various qualitative and/or quantitative characteristics associated with test organisms of each group, or combinations thereof.

In an embodiment, assessing the acceptability of the fluid and/or the fluid component may further comprise comparing the control group with the test groups. In various embodiments, the control group and the test groups may be compared to determine whether any statistically significant difference, in any one or more of the observed characteristics, qualities, or quantities, may be due to the presence of the wellbore servicing fluid or any component thereof at any of the tested concentrations. In an embodiment, various statistical methods may be employed to determine the significance of any apparent or unapparent difference between the control group and any one or more of the test groups.

In an embodiment, the wellbore servicing fluid and/or a component thereof may be deemed acceptable where no statistically significant difference exists between the control group and one or more of the test groups, depending upon the test group. For example, a wellbore servicing fluid and/or component may be deemed acceptable for use at some concentrations and unacceptable at other concentrations. Alternatively, the wellbore servicing fluid and/or a component thereof may be deemed acceptable where the differences between the control group and one or more of the test groups are not detrimental to the test organisms (e.g., where the wellbore servicing fluid and/or component has a beneficial effect on the test organisms).

In various embodiments, assessing the acceptability of the fluid and/or the fluid component may comprise determining a median lethal concentration (an $LC_{50}$), a median effective concentration (an $EC_{50}$), an inhibitory concentration (an $IC_{50}$), a no observed effect concentration (NOEC), a lowest observed effect concentration (a LOEC), or combinations thereof. As used herein, the term "$LC_{50}$" may refer to the concentration of a test substance where 50% of the organisms die; the term "$EC_{50}$" may refer to the concentration of a test substance where 50% of the organisms show a significant given effect (e.g., if a skin test, where half the organisms show the expected rash or response); the term "$IC_{50}$" may refer to the concentration of a test substance where 50% of the organisms given response is inhibited (e.g., where production stops); the term "NOEC" may refer to the highest concentration where no significant effect is observed; and the term "LOEC" may refer to the lowest concentration where some significant effect is observed.

In an embodiment, where the wellbore servicing fluid or various components thereof are deemed acceptable for usage, the wellbore servicing fluid or component may be made available for usage. For example, a provider or manufacturer may package the fluid and/or fluid component for distribution and usage by an end user. Such a provider or manufacturer may provide instructions, information, and/or recommendations (e.g., on, within, or included with the product) for the safe and proper usage of the fluid or fluid component. For example, such instructions, information, or recommendations may include safe and effective concentrations for usage, geographical or other usage restrictions, proposed risk avoidance measures, proposed clean-up procedures, safety and/or environmental impact ratings, or the like.

In an embodiment, where the wellbore servicing fluid or various components thereof are deemed acceptable for usage, the wellbore servicing fluid, alternatively, the acceptable wellbore servicing fluid components, may be utilized in a wellbore servicing operation. In such an embodiment, the wellbore servicing operation may comprise a drilling operation, a wellbore clean-out operation, a completion and/or cementing operation, an acidizing operation, a perforating operation, a fracturing or other stimulation operation, a workover operation, a shut-in or well-kill operation, any other like, suitable operation, as will be recognized by one of skill in the art viewing this disclosure, or combinations thereof.

In an embodiment, the wellbore servicing fluid may be prepared at the site of such a servicing operation (e.g., at the wellhead). For example, the wellbore servicing fluid and/or component may be mixed (e.g., via the operation of one or more blenders) one or more additional component in suitable amounts to yield a servicing fluid of a desired character. In an alternative embodiment, the wellbore servicing fluid or component may be prepared off-site and transported to the work site.

In an embodiment, the prepared wellbore servicing fluid may be conveyed into the wellbore and/or into the subterranean formation. For example, the prepared fluid present at the work site may be conveyed via the operation of one or more pumps, compressors, or the like, through flowlines (e.g., manifolds, tubing, etc.) into the wellbore. As will be appreciate by one of skill in the art the wellbore servicing fluid may be conveyed at a suitable rate and/or pressure, as may depend upon the particular servicing operation being performed. In addition, the wellbore servicing fluid may be circulated through the wellbore, introduced into the formation (e.g., a fracture or perforation within the formation), or to a predetermined depth within the wellbore.

In various embodiments, the wellbore servicing operation may be directed to a wellbore penetrating a subterranean formation beneath dry land, alternatively, to a subterranean formation beneath a body of water.

ADDITIONAL DISCLOSURE

The following are non-limiting, specific embodiments in accordance with the present disclosure:

Embodiment 1. A method of assessing a wellbore servicing fluid or a component thereof comprising:
  providing a plurality of test organisms, wherein providing the plurality of test organisms comprises:
    introducing at least a portion of a population of the test organisms into a first section of a first tub, wherein the first section of the first tub is separated from a second section of the first tub by a first screen, wherein the first screen is configured to retain an organism of at least a first size and to allow passage of an organism less than the first size;
    allowing at least a portion of the organisms of a size less than the first size to pass through the first screen and into the second section of the first tub;
    allowing at least a portion of the organisms of a size less than the first size to flow out of the first tub and into a first section of a second tub, wherein the first section of the second tub is separated from a second section of the second tub by a second screen, wherein the second screen is configured to retain an organism of at least a second size and to allow passage of an organism less than the second size;
    allowing at least a portion of the organisms of a size less than the second size to pass through the second screen and into the second section of the second tub;
    allowing at least a portion of the organisms of a size less than the second size to flow out of the second tub and into a first section of a third tub, wherein the first section of the third tub is separated from a second section of the third tub by a third screen, wherein the third screen is configured to retain an organism of at least a third size and to allow passage of an organism less than the third size;

allowing at least a portion of the organisms of a size less than the third size to pass through the third screen and into the second section of the third tub; and allowing at least a portion of the organisms of a size less than the third size to flow out of the third tub;

selecting test organisms of a size desired for testing from the first section of the first tub, the first section of the second tub, the first section of the third tub, or combinations thereof;

dividing the test organisms of the selected size into a control group and at least one test group;

subjecting the at least one test group to the wellbore servicing fluid or component thereof; and assessing the acceptability of the wellbore servicing fluid or component thereof.

Embodiment 2. The method of claim 1, wherein providing the plurality of test organisms further comprises:

allowing at least a portion of the organisms of the size less than the third size to flow out of the third tub and into a first section of a fourth tub, wherein the first section of the fourth tub is separated from a second section of the fourth tub by a fourth screen, wherein the fourth screen is configured to retain an organism of at least a fourth size and to allow passage of an organism less than the fourth size;

allowing at least a portion of the organisms of a size less than the fourth size to pass through the fourth screen and into the second section of the fourth tub; and allowing at least a portion of the organisms of a size less than the fourth size to flow out of the fourth tub.

Embodiment 3. The method of embodiment 2, wherein the first screen comprises a mesh size of about 1,000 microns, the second screen comprises a mesh size of about 710 microns, the third screen comprises a mesh size of about 500 microns, and the fourth screen comprises a mesh size of about 300 microns.

Embodiment 4. The method of embodiment 2, wherein at least a portion of the test organisms retained in the second section of the first tub have a size of about greater than about 1,000 microns, wherein at least a portion of the test organisms retained in the second section of the second tub have a size of from about 710 microns to about 1,000 microns, wherein at least a portion of the test organisms retained in the second section of the third tub have a size of from about 500 microns to about 710 microns, and wherein at least a portion of the test organisms retained in the second section of the fourth tub have a size from about 300 microns to about 500 microns.

Embodiment 5. The method of embodiment 2, wherein providing the plurality of test organisms further comprises:

allowing at least a portion of the organisms of the size less than the fourth size to flow out of the fourth tub and into a first section of a fifth tub, wherein the first section of the fifth tub is separated from a second section of the fifth tub by a fifth screen, wherein the fifth screen is configured to retain an organism of at least a fifth size and to allow passage of an organism less than the fifth size;

allowing at least a portion of the organisms of a size less than the fifth size to pass through the fifth screen and into the second section of the fifth tub; and allowing at least a portion of the organisms of a size less than the fifth size to flow out of the fourth tub.

Embodiment 6. The method of embodiment 5, wherein the first screen comprises a mesh size of about 1,000 microns, the second screen comprises a mesh size of about 850 microns, the third screen comprises a mesh size of about 710 microns, the fourth screen comprises a mesh size of about 500 microns, and the fifth screen comprises a mesh size of about 300 microns.

Embodiment 7. The method of embodiment 5, wherein at least a portion of the test organisms retained in the second section of the first tub have a size of about greater than about 1,000 microns, wherein at least a portion of the test organisms retained in the second section of the second tub have a size of from about 850 microns to about 1,000 microns, wherein at least a portion of the test organisms retained in the second section of the third tub have a size of from about 710 microns to about 850 microns, wherein at least a portion of the test organisms retained in the second section of the fourth tub have a size from about 500 microns to about 710 microns, and wherein at least a portion of the test organisms retained in the second section of the fifth tub have a size of from about 300 microns to about 500 microns.

Embodiment 8. The method of embodiment 2, wherein the first tub is positioned at a height greater than the height at which the second tub is positioned, wherein the second tub is positioned at a height greater than the height at which the third tub is positioned, and wherein the third tub is positioned at a height greater that the height at which the fourth tub is positioned.

Embodiment 9. The method of embodiment 5, wherein the first tub is positioned at a height greater than the height at which the second tub is positioned, wherein the second tub is positioned at a height greater than the height at which the third tub is positioned, wherein the third tub is positioned at a height greater that the height at which the fourth tub is positioned, and wherein the fourth tub is positioned at a height greater than the height at which the fifth tub is positioned.

Embodiment 10. The method of one or more of embodiments 1 through 9, wherein one or more of the first screen, the second screen, or the third screen comprises a sieve.

Embodiment 11. The method of one or more of embodiments 1 through 10, wherein one or more of the first screen, the second screen, or the third screen comprises a wall.

Embodiment 12. The method of one or more of embodiments 1 through 11, wherein the first tub further comprises a valve and a flow conduit in fluid communication with the second section of the first tub, wherein the portion of the organisms of less than the first size are allowed to flow out of the first tub and into the first section of a second tub via the valve and the flow conduit.

Embodiment 13. The method of embodiment 2, wherein the test organisms are introduced within an aquatic solution, wherein the aqueous solution comprises sediment.

Embodiment 14. The method of embodiment 13, wherein the aqueous solution comprises a salinity of about 20%.

Embodiment 15. The method of one or more of embodiments 1 through 14, wherein the at least one test group comprises at least two test groups, wherein, in each of the at least two test groups, the test organisms are subjected to the wellbore servicing fluid or component thereof at varying concentrations.

Embodiment 16. The method of one or more of embodiments 1 through 15, wherein the at least one test group comprises at least two test groups, wherein, in each of the at least two test groups, the test organisms are subjected to a different component of the wellbore servicing fluid.

Embodiment 17. The method of one or more of embodiments 1 through 16, wherein the test organism comprises *Leptocheirus plumulosus*.

Embodiment 18. The method of one or more of embodiments 1 through 17, wherein the test organisms selected for testing are of a size from about 710 microns to about 1000 microns.

Embodiment 19. The method of one or more of embodiments 1 through 18, wherein the test organisms selected for testing are of a size from about 710 microns to about 850 microns.

Embodiment 20. The method of one or more of embodiments 1 through 19, wherein wellbore servicing fluid comprises a drilling fluid, a perforating fluid, a fracturing fluid, an acidizing fluid, or a cementitious composition.

At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, Rl, and an upper limit, Ru, is disclosed, any number falling within the range is specifically disclosed. In particular, the following numbers within the range are specifically disclosed: R=Rl+k*(Ru−Rl), wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim means that the element is required, or alternatively, the element is not required, both alternatives being within the scope of the claim. Use of broader terms such as comprises, includes, and having should be understood to provide support for narrower terms such as consisting of, consisting essentially of, and comprised substantially of. Accordingly, the scope of protection is not limited by the description set out above but is defined by the claims that follow, that scope including all equivalents of the subject matter of the claims. Each and every claim is incorporated as further disclosure into the specification and the claims are embodiment(s) of the present invention.

What is claimed is:

1. A method of assessing a wellbore servicing fluid or a component thereof comprising:
   providing a plurality of test organisms, wherein providing the plurality of test organisms comprises:
      introducing at least a portion of a population of the test organisms into a first section of a first tub, wherein the first section of the first tub is separated from a second section of the first tub by a first screen, wherein the first screen is configured to retain an organism of at least a first size and to allow passage of an organism less than the first size;
      allowing at least a portion of the organisms of a size less than the first size to pass through the first screen and into the second section of the first tub;
      allowing at least a portion of the organisms of a size less than the first size to flow out of the first tub and into a first section of a second tub, wherein the first section of the second tub is separated from a second section of the second tub by a second screen, wherein the second screen is configured to retain an organism of at least a second size and to allow passage of an organism loss than. the second size;
      allowing at least a portion of the organisms of as size less than the second size to pass through the second screen and into the second section of the second tub;
      allowing at least a portion of the organisms of a size less than the second size to flow out of the second tub and into a first section of a third tub, wherein the first section of the third tub is separated from a second section of the third tub by a third screen, wherein the third screen is configured to retain organism of at least a third size and to allow passage of an organism less than the third size;
      allowing at least a portion of the organisms of a size less than the third size to pass through the third screen and into the second section of the third tub; and
      allowing at least a portion of the organisms of a size less than the third size to flow out of the third tub;
   selecting test organisms for testing from the first section of the first tub, the first section of the second tub, the first section of the third tub, or combinations thereof;
   dividing the selected test organisms into a control group and at least one test group;
   subjecting the at least one test group to the wellbore servicing fluid or component thereof; and
   assessing the acceptability of the wellbore servicing fluid or component thereof.

2. The method of claim 1, wherein providing the plurality of test organisms further comprises:
   allowing at least a portion of the organisms of a size less than the third size to flow out of the third tub and into a first section of a fourth tub, wherein the first section of the fourth tub is separated from a second section of the fourth tub by a fourth screen, wherein the fourth screen is configured to retain an organism of at least a fourth size and to allow passage of an organism less than the fourth size;
   allowing at least a portion of the organisms of a size less than the fourth size to pass through the fourth screen and into the second section of the fourth tub; and
   allowing at least a portion of the organisms of a size less than the fourth size to flow out of the fourth tub.

3. The method of claim 2, wherein the first screen comprises a mesh size of about 1,000 microns, the second screen comprises a mesh size of about 710 microns, the third screen comprises a mesh size of about 500 microns, and the fourth screen comprises a mesh size of about 300 microns.

4. The method of claim 2, wherein at least portion of the test organisms retained in the second section of the first tub have a size of greater than about 1,000 microns, wherein at least a portion of the test organisms retained in the second section of the second tub have a size of from about 710 microns to about 1,000 microns, wherein at least a portion of the test organisms retained in the second section of the third tub have as size of from about 500 microns to about 710 microns, and wherein at least a portion of the test organisms retained in the second section of the fourth tub have a size from about 300 microns to about 500 microns.

5. The method of claim 2, wherein providing the plurality of test organisms further comprises:

allowing at least a portion of the organisms of a size less than the fourth size to flow out of the fourth tub and into a first section of a fifth tub, wherein the first section of the fifth tub is separated from a second section of the fifth tub by a fifth screen, wherein the fifth screen is configured to retain an organism of at least a fifth size and to allow passage of an organism less than the fifth size;

allowing at least a portion of the organisms of a size less than the fifth size to pass through the fifth screen and into the second section of the fifth tub; and allowing at least a portion of the organisms of a size less than the fifth size to flow out of the fifth tub.

6. The method of claim 5, wherein the first screen comprises a mesh size of about 1,000 microns, the second screen comprises a mesh size of about 850 microns, the third screen comprises a mesh size of about 710 microns, the fourth screen comprises a mesh size of about 500 microns, and the fifth screen comprises a mesh size of 300 microns.

7. The method of claim 5, wherein at least a portion of the test organisms retained in the second section of the first tub have a size of greater than about 1,000 microns, wherein at least a portion of the test organisms retained in the second section of the second tub have a size of from about 850 microns to about 1,000 microns, wherein at least a portion of the test organisms retained in the second section of the third tub have a size of from about 710 microns to about 850 microns, wherein at least a portion of the test organisms retained in the second section of the fourth tub have a size from about 500 microns to about 710 microns, and wherein at least a portion of the test organisms retained in the second section of the fifth tub have a size of from about 300 microns to about 500 microns.

8. The method of claim 2, wherein he first tub is positioned at a height greater than the height at which the second tub is positioned, wherein the second tub is positioned at a height greater than the height at which the third tub is positioned, and wherein the third tub is positioned at a height greater than the height at which the fourth tub is positioned.

9. The method of claim 5, wherein the first tub is positioned at a height greater than the height at which the second tub is positioned, wherein the second tub is positioned at a height greater than the height at which the third tub is positioned, wherein the third tub is positioned at a height greater than the height at which the fourth tub is positioned, and wherein the fourth tub is positioned at a height grater than the height at which the fifth tub is positioned.

10. The method of claim 1, wherein one or more of the first screen, the second screen, or the third screen comprises a sieve.

11. The method of claim wherein one or more of the first screen, the second screen, or the third screen comprises a wall.

12. The method of claim 1, wherein the first tub further comprises a valve and a flow conduit in fluid communication with the first section of the second tub, wherein the portion of the organisms of less than the first size are allowed to flow out of the first tub and into the first section of the second tub via the valve and the flow conduit.

13. The method of claim 2, wherein the test organisms are introduced within an aquatic solution, wherein the aqueous solution comprises sediment.

14. The method of claim 13, wherein the aqueous solution comprises a salinity of about 20%.

15. The method of claim 1, wherein the at least one test group comprises at least two test groups, wherein, in each of the at least two test groups, the test organisms are subjected to the wellbore servicing fluid or component thereof at varying concentrations.

16. The method of claim 1, herein the at least one test group comprises at least two test groups, wherein, in each of the at least two test groups, the test organisms are subjected to a different component of the wellbore servicing fluid.

17. The method of claim 1, wherein the test organisms comprise *Lepocheirus plumulosus*.

18. The method of claim 1, wherein the test organisms selected for testing are of a size from about 710 microns to about 1000 microns.

19. The method of claim 1, wherein the test organisms selected for testing are of a size from about 710 microns to about 850 microns.

20. The method of claim 1, wherein the wellbore servicing fluid comprises a drilling fluid, a perforating fluid, as fracturing fluid, an acidizing fluid, or a cementitious composition.

* * * * *

UNITED STATES PATENT AND TRADEMARK OFFICE
CERTIFICATE OF CORRECTION

| | | |
|---|---|---|
| PATENT NO. | : 9,435,182 B2 | |
| APPLICATION NO. | : 13/527373 | |
| DATED | : September 6, 2016 | |
| INVENTOR(S) | : Jeanie Lynn Lawson Mohar | |

It is certified that error appears in the above-identified patent and that said Letters Patent is hereby corrected as shown below:

In the Claims

In Column 18, line 11, change "loss than." to --less than--;
In Column 18, line 12, change "as" to --a--;
In Column 18, line 20, "retain organism" should read --retain an organism--;
In Column 20, line 5, change "grater" to --greater--.

Signed and Sealed this
Twenty-ninth Day of November, 2016

Michelle K. Lee
*Director of the United States Patent and Trademark Office*